United States Patent [19]
Kerr

[11] Patent Number: 5,439,471
[45] Date of Patent: Aug. 8, 1995

[54] COMBINED SURGICAL NEEDLE HOLDER AND SCISSORS

[76] Inventor: Harry D. Kerr, 4641 N. Ardmore Ave., Whitefish Bay, Wis. 53211

[21] Appl. No.: 177,599

[22] Filed: Jan. 5, 1994

[51] Int. Cl.⁶ .............................................. A61B 17/06
[52] U.S. Cl. .................................... 606/174; 606/205
[58] Field of Search ................ 606/174, 172, 205, 207

[56] References Cited

U.S. PATENT DOCUMENTS

| | | | |
|---|---|---|---|
| 2,315,326 | 3/1943 | Gmeiner | 606/174 X |
| 4,271,838 | 6/1981 | Lasner et al. | 128/318 |
| 4,452,246 | 6/1984 | Bader et al. | 606/174 X |
| 4,452,246 | 6/1984 | Bader et al. | 128/340 |
| 5,002,554 | 3/1991 | Korber | 606/174 |
| 5,171,258 | 12/1992 | Bales et al. | 606/205 |

FOREIGN PATENT DOCUMENTS 647935  7/1937  Germany .

OTHER PUBLICATIONS

"Emergency Physician's Needle Holder", Abidin et al, The Journal of Emergency Medicine, vol. 7, pp. 581–585, 1989.

Primary Examiner—Stephen C. Pellegrino
Assistant Examiner—Nancy Mulcare
Attorney, Agent, or Firm—Andrus, Sceales, Starke & Sawall

[57] ABSTRACT

A combined surgical needle holder and scissors to be used in suturing procedures. The instrument includes a pair of arms which are pivotally connected together at a location intermediate their ends. A flat clamping jaw is associated with each arm and is spaced from a first end of the arm. As the arms are pivoted, the jaws are brought into clamping relation to clamp a surgical needle. A scissors blade is formed on each arm and is located between the clamping jaw and the distal end of the arm. The scissor blades are constructed to be moved into overlapping cutting relation when the distal ends of the arms are moved toward each other.

10 Claims, 1 Drawing Sheet

COMBINED SURGICAL NEEDLE HOLDER AND SCISSORS

BACKGROUND OF THE INVENTION

In a typical suturing procedure, the suture needle is manipulated through either the skin or underlying tissue of a laceration, by use of a surgical needle holder. With the needle secured in the jaws of the needle holder, the needle holder serves to guide the needle, causing the needle to pierce the skin adjacent the laceration, so that the edges of the laceration may be drawn together by the suturing thread which is bonded to the needle. In this manner, the thread serves to close the laceration and the thread is then tied by a surgeon's knot. With interrupted suturing, the suture thread is cut after each suture, so that the sutures are physically separate from one another.

Suturing of simple lacerations, particularly lacerations of the face and hands, comprise a substantial proportion of patients seen in emergency departments, urgent care centers and family practitioner's offices. Lacerations of this type usually require one or two layers of sutures for adequate repair, and the typical laceration usually has a length of 0.5 to 5.0 cm.

The physician suturing a simple laceration works without an assistant, and accordingly, the suturing procedure is tedious, redundant, and time-consuming. By contrast, in the operating room setting, an assistant will pass instruments, cut sutures in rhythm with their placement, retract wound edges, and perform other small, but time-consuming tasks.

In the usual sequence of suturing a simple laceration, the curved needle is clamped by the needle holder held in one hand by the surgeon, and the needle with thread attached is passed through both wound edges. The needle, after passing through the wound edges is then grasped either with the surgeon's fingers or a forceps and held in the opposite hand. The needle holder is then used to tie the surgeon's knot, and the suture is then cut. In the normal procedure, it is necessary for the surgeon to place the needle holder on the instrument tray and pick up the scissors in order to cut the suture. After cutting the suture, the scissors are placed back on the tray and the needle holder again picked up and the suturing process repeated. A simple cm laceration often requires a number of sutures, and if the wound is deep, it may also include the placement of buried absorbable sutures prior to placement of the skin sutures. Thus, even when suturing minor lacerations, multiple picking up and putting down of instruments is required. This not only is time consuming, but creates a measure of distraction for the surgeon from the performance of the surgical process.

As a further problem, the continual picking up and putting down of instruments on the surgical tray presents opportunities for possible injury to the surgeon due to accidental cuts or needle sticks. This is of major importance in accidental transmission of certain blood-borne diseases.

In an attempt to avoid the sequences of instrument transfers, it has been proposed to utilize an instrument which combines both a needle holder and scissors, such as shown in U.S. Pat. No. 2,315,326. In the instrument as disclosed in that patent, a pair of opposing clamping jaw surfaces are provided at the distal end of each arm of the instrument and working surfaces shaped as a pair of blades are located between the clamping jaws and the pivot axis of the arms.

A combined needle holder and scissors of that type has certain drawbacks. As the scissor blades are located inwardly from the distal end of the arms of the instrument, it obscures the surgeon's view of cutting. As a further disadvantage, the scissors can only be used for cutting the suture thread and cannot normally be used for trimming tissue and debriding small bits of a wound. In addition, with the scissors located inwardly of the clamping jaws, no scissor points or tips define the scissors, so that it is difficult for the surgeon to precisely locate the scissor blades.

It has also been proposed in the past to design a combined needle holder and scissors with a third arm, as shown in U.S. Pat. 4,452,246. In this construction, the third arm contains a scissors blade which operates against the outer edge of the needle holder to provide a cutting function. However, instruments of this type, incorporating a third arm, are more costly to produce and are more cumbersome and difficult to manipulate.

SUMMARY OF THE INVENTION

The invention is directed to an improved surgical instrument, and more particularly to a combined surgical needle holder and scissors. The instrument includes a pair of arms which are pivotally connected together intermediate their length so that the arms are in an X-shaped configuration. A generally flat clamping jaw surface is located on each arm and spaced from the distal end of the arm. As the distal ends of the arms are pivoted toward each other, the clamping jaw surfaces will be moved to a clamping position to clamp a suture needle.

The portion of each arm located between the clamping jaw surface and the distal end is formed with a scissors blade, and as the distal ends are pivoted toward each other, the blades move into an overlapping cutting relation, so that they can be used to cut the suture thread.

In the preferred form of the invention, a small transition zone separates the scissor blades from the clamping jaw surfaces and the transition zone provides a visual separation between the scissors and clamping jaws, which minimizes the possibility of the scissors accidentally grasping and severing the thread while tying a knot with the instrument.

In addition, the scissors are blunt tipped to avoid accidentally slashing the patient during suturing.

Incorporating the scissors with the needle holder in one instrument eliminates the sequence of instrument transfer which has been necessary in the past when utilizing separate needle holders and scissors.

As the transfer or exchange of instruments is minimized, the likelihood of dropping instruments on the floor, spilling solutions on the surgical tray, or surgeon injuries due to accidental contact with sharp instruments on the tray are substantially reduced.

Positioning the scissors at the distal tip of the instrument enables the scissors to be used for other operations in addition to cutting of the suture thread, as for example, trimming minor amounts of tissue, enlarging the fenestration of a paper drape, and the like.

As the scissors are located at the tip of the instrument, an unobstructed view is obtained during the cutting operation and permits use in trimming deeper sutures which can be accomplished only with great difficulty when using a combination needle holder and scissors in which the needle clamping surfaces are located at the distal end of the instrument.

Other objects and advantages will appear in the course of the following description.

DESCRIPTION OF THE DRAWINGS

The drawings illustrate the best mode presently contemplated of carrying out the invention.

In the drawings.

DESCRIPTION OF THE ILLUSTRATED EMBODIMENT

The drawings illustrate a surgical instrument and in particular an improved combination surgical needle holder and scissors.

Figure 1:
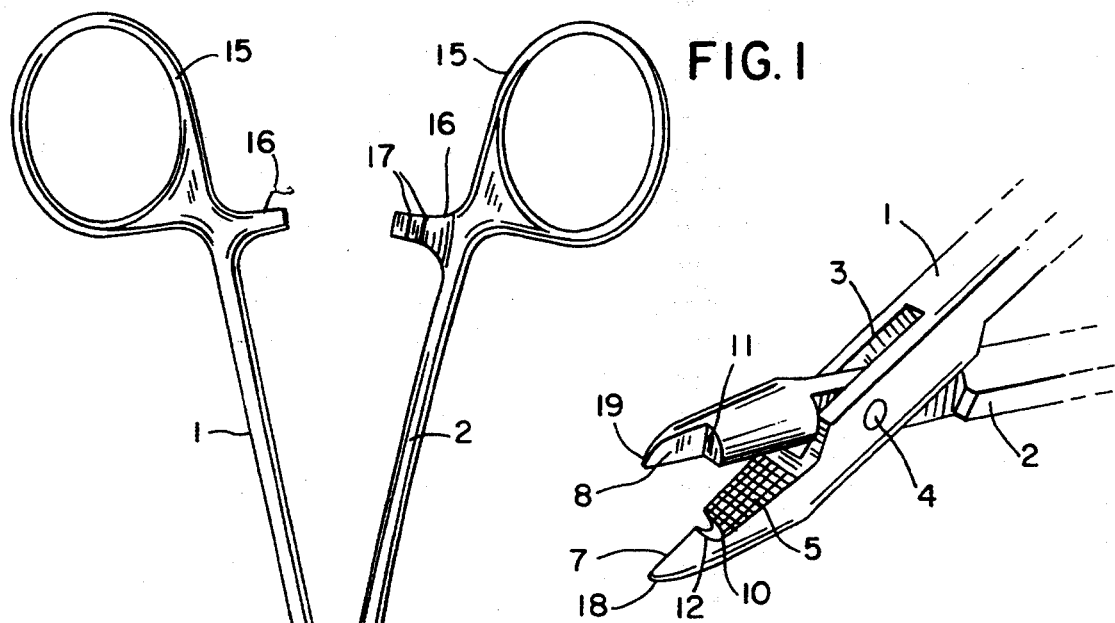
FIG. 1 is a plan view of the surgical instrument of the invention.
Figure 2:
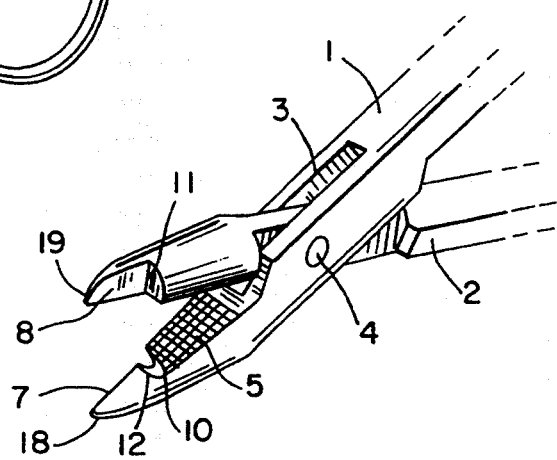
FIG. 2 is a fragmentary perspective view of the distal end portion of the instrument with the distal ends being shown in an open position.
Figure 4:
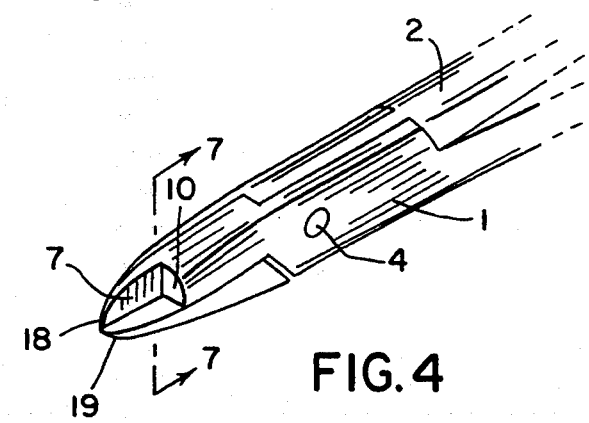
FIG. 4 is a view similar to FIG. 3 showing the distal ends of the arms of the instrument in a closed position.
Figure 5:
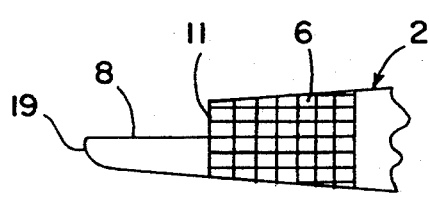
FIG. 5 is a fragmentary plan view of the distal end of one of the arms.

The instrument includes a pair of elongated arms 1 and 2, and arm 1 is provided with an elongated slot 3 which receives the arm 2. Arms 1 and 2 are pivotally connected together at a pivot 4, so that the distal ends of the arms can be pivoted between an open position, as shown in FIG. 2, and a closed position as shown in FIG. 4.

Arm 1 is provided with a flat, clamping surface 5 which is spaced inwardly from the distal end of the arm. Similarly, arm 2 is formed with a flat clamping surface 6 also spaced from the distal end of the arm. When the distal ends of the arms are moved to the closed position, as seen in FIG. 4, the clamping surfaces 5 and 6 will be brought into contiguous flatwise relation to thereby clamp a needle between the surfaces.

Surfaces 5 and 6 are preferably roughened to provide more effective clamping of the needle and, as shown in the drawings, the roughened surface can be achieved by serrations or grooves.

Figure 3:
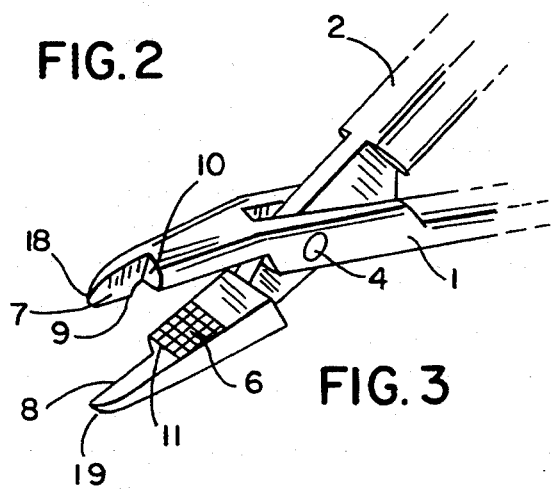
FIG. 3 is a fragmentary perspective view of the distal end of the instrument, with the instrument being inverted with respect to FIG. 2.

A scissor surface 7 is formed on arm 1 between the clamping surface 5 and the distal end of the arm. Scissor surface 7 is disposed perpendicular or normal to clamping surface 5, as shown in FIG. 3.

Arm 2 is also formed with a scissor surface 8 that is located normal to clamping surface 6, and when the distal ends of the arms are pivoted to the closed position, the scissor surfaces 7 and 8 will be in an overlapping cutting position, so that they can be used to sever the suture thread.

To provide the overlapping relation between the scissor surfaces 7, 8, surface 7 is provided with an extension 9 which is in overlapping relation with surface 8 when the distal ends of the arms are pivoted to the closed position. While the drawings shown the extension 9 being formed on only one of the scissor blade surfaces, it is contemplated that extensions could be formed on both of the scissor blade surfaces.

The outer extremity of clamping surface 5 is bordered by a shoulder 10 and similarly, the outer extremity of clamping surface 6 is bordered by a shoulder 11. Shoulders 10 and 11 are located normal to the longitudinal dimensions of the respective arm.

Figure 6:
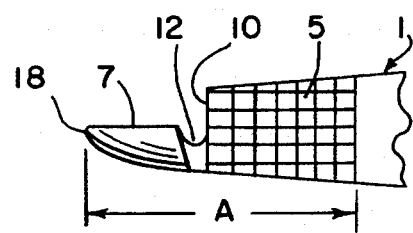
FIG. 6 is a fragmentary plan view of the distal end of the other of the arms.
Figure 7:
FIG. 7 is a section taken along line 7—7 of FIG. 4.

As seen in FIG. 6, a transition zone 12 is located between the blade surface 7 and the clamping surface 5. Transition zone 12 comprises a groove or undercut and provides a visual separation between the scissors and the clamping jaws to enable the surgeon to more precisely utilize the clamping and scissor functions.

The end of each arm 1 and 2 is provided with a standard finger loop 15, and to lock the arms in the clamping position, projections 16 extend laterally from each arm, and the projections are formed with parallel serrations or grooves 17. When the ends of the arms containing finger loops 15 are brought together, the serrations 17 on the projections 16 will move into engaging relation to thereby hold or lock the arms in the clamping position.

In the preferred form of the invention, the scissor blade surfaces 7 and 8 extend about 30% to 40% of the combined length of the blade surfaces and the clamping surfaces (length A in FIG. 6). Thus, the short length of the scissors will not obscure the surgeon's view when using the clamping jaws to clamp the needle and maneuver the needle through the skin or tissue.

The distal ends or tips 18 and 19 of arms 1 and 2 are rounded or blunt to prevent accidentally cutting or slashing the patient during suturing.

The transition zone 12 provides a visual separation between the scissors and needle holder which minimizes the possibility of the scissors accidentally grasping and severing the thread while tying a knot with the instrument.

As the scissors blades 7 and 8 are located at the tip of the instrument, there is no obstruction to the surgeon's view while cutting the suture thread. Positioning the scissor blades at the tip of the instrument also enables the scissors to be used in trimming deeper sutures and further permits routine sharpening of the blades 7 and 8.

As the scissors and needle holder are combined in a single instrument, fewer exchanges of instruments are required during the suturing procedure, which lessens the likelihood of dropping the instruments and minimizes possible injury to the surgeon due to accidental contact with sharp objects on the surgical tray during transfer of the instruments.

Various modes of carrying out the invention are contemplated as being within the scope of the following claims particularly pointing out and distinctly claiming the subject matter which is regarded as the invention.

I claim:

1. A surgical instrument, comprising a pair of elongated arms, each arm having a first end and a second end, pivot means for pivoting the arms together at a location intermediate said first and second ends, whereby said first ends are movable between a closed position where said ends are in proximate relation to each other and an open position where said first ends are spaced apart, a generally flat clamping jaw surface disposed on each arm and spaced from the first end of said arm, said clamping jaw surfaces being disposed in flatwise contiguous relation when said first ends are in the closed position, and a scissor blade disposed on each arm and located between the corresponding clamping surface and said first end, said blades being constructed and arranged to be in overlapping cutting relation when said first ends are in the closed position.

2. The instrument of claim 1, and including a shoulder disposed between each clamping surface and the corresponding blade.

3. The instrument of claim 2, wherein each shoulder is disposed normal to the longitudinal dimension of the arm.

4. The instrument of claim 1, wherein a portion of at least one of the arms located between the scissor blade and the corresponding clamping surface is undercut to provide a visual transition zone.

5. The instrument of claim 1, and including locking means interconnecting the arms for locking the first ends in the closed position.

6. The instrument of claim 5, wherein said locking means comprises a projection on each arm and extending laterally from said arm toward the opposite arm, and a plurality of serrations on each arm, said serrations being disposed to be in engaging relation when said first ends are in the closed position to thereby lock the arms together.

7. The instrument of claim 1, wherein said first ends are blunt.

8. A surgical instrument, comprising a pair of elongated arms, each arm having a first end and a second end, pivot means for pivoting the arms together at a location intermediate said first and second ends, whereby said first ends are movable between a closed position where said first ends are in proximate relation to each other and an open position where said first ends are spaced apart, a generally flat clamping surface disposed on each arm and spaced from the first end of said arm, said clamping surfaces being constructed and arranged to be in flatwise contiguous relation when said first ends are in the closed position to thereby clamp an object therebetween, and a scissor blade disposed on each arm and located between the corresponding clamping surface and said first end, each scissor blade disposed generally normal to the corresponding clamping surface, at least one of said blades extending laterally beyond the corresponding clamping surface to overlap the other blade when said first ends are in the closed position, a portion of at least one of said arms between the scissor blade and the corresponding clamping surface being undercut to provide a visual transition zone.

9. The instrument of claim 8, wherein the end of each clamping surface facing the corresponding scissor blade terminates in a shoulder disposed normal to the longitudinal dimension of the arm.

10. A surgical instrument, comprising a pair of elongated arms, each arm having a first end and a second end, pivot means for pivoting the arms together at a location intermediate said first and second ends, whereby said first ends are movable between a closed position where said first ends are in proximate relation to each other and an open position where said first ends are spaced apart, a generally flat clamping surface disposed on each arm and spaced longitudinally from the first end of said arm, said clamping surfaces being constructed and arranged to be in a flat-wise contiguous relation when said first ends are in the closed position to thereby clamp an object therebetween, and a scissor blade disposed on each arm and located between the corresponding clamping surface and said first end, each scissor blade disposed generally normal to the corresponding clamping surface and at least one of said scissor blades extending laterally beyond the corresponding clamping surface to overlap the other scissor blade when said first ends are in the closed position.

* * * * *